US009933407B2

(12) United States Patent
Brigmon et al.

(10) Patent No.: US 9,933,407 B2
(45) Date of Patent: Apr. 3, 2018

(54) WATER COOLER TOWERS AND OTHER MAN-MADE AQUATIC SYSTEMS AS ENVIRONMENTAL COLLECTION SYSTEMS FOR AGENTS OF CONCERN

(75) Inventors: Robin Brigmon, North Augusta, SC (US); Mark T. Kingsley, Aiken, SC (US)

(73) Assignee: SAVANNAH RIVER NUCLEAR SOLUTIONS, LLC, Aiken, SC (US)

(*) Notice: Subject to any disclaimer, the term of this patent is extended or adjusted under 35 U.S.C. 154(b) by 98 days.

(21) Appl. No.: 13/311,765

(22) Filed: Dec. 6, 2011

(65) Prior Publication Data
US 2012/0137756 A1 Jun. 7, 2012

Related U.S. Application Data

(60) Provisional application No. 61/459,102, filed on Dec. 7, 2010.

(51) Int. Cl.

*G01N 33/18* (2006.01)
*C12Q 1/04* (2006.01)
*G01N 1/02* (2006.01)
*G01N 1/22* (2006.01)

(52) U.S. Cl.

CPC ............... *G01N 33/18* (2013.01); *C12Q 1/04* (2013.01); *G01N 2001/021* (2013.01); *G01N 2001/022* (2013.01); *G01N 2001/2217* (2013.01); *G01N 2333/32* (2013.01)

(58) Field of Classification Search

USPC ........... 73/61.59, 61.72, 28.01–28.06, 31.01, 73/31.05, 31.07; 96/240

See application file for complete search history.

(56) References Cited

U.S. PATENT DOCUMENTS

| | | | | |
|---|---|---|---|---|
| 4,094,937 | A | 6/1978 | Bodick et al. | |
| 4,243,095 | A | 1/1981 | Kosten | |
| 5,383,337 | A | 1/1995 | Baker | |
| 6,607,669 | B2 * | 8/2003 | Schick | 210/637 |
| 2005/0284300 | A1 * | 12/2005 | Marusic | 96/271 |
| 2006/0109344 | A1 * | 5/2006 | Maurer et al. | 348/82 |
| 2008/0237142 | A1 * | 10/2008 | Carpenter et al. | 210/741 |

OTHER PUBLICATIONS

Hensley, J. C. (Ed.). (Nov. 29, 2010). Cooling Tower Fundamentals. Retrieved Jul. 14, 2016, from http://spxcooling.com/pdf/Cooling-Tower-Fundamentals.pdf.*

* cited by examiner

*Primary Examiner* — Peter Macchiarolo
*Assistant Examiner* — Alexander Mercado
(74) *Attorney, Agent, or Firm* — J. Bennett Mullinax, LLC

(57) ABSTRACT

An apparatus and process of using existing process water sources such as cooling towers, fountains, and waterfalls is provided in which the water sources are utilized as monitoring system for the detection of environmental agents which may be present in the environment. The process water is associated with structures and have an inherent filtering or absorbing capability available in the materials and therefore can be used as a rapid screening tool for quality and quantitative assessment of environmental agents.

10 Claims, 5 Drawing Sheets

WATER COOLER TOWERS AND OTHER MAN-MADE AQUATIC SYSTEMS AS ENVIRONMENTAL COLLECTION SYSTEMS FOR AGENTS OF CONCERN

RELATED APPLICATIONS

This application claims the benefit of U.S. Provisional Patent Application Ser. No. 61/459,102, filed on Dec. 7, 2010, and which is incorporated herein by reference for all purposes.

STATEMENT AS TO RIGHTS TO INVENTIONS MADE UNDER FEDERALLY SPONSORED RESEARCH AND DEVELOPMENT

This invention was made with Government support under Contract No. DE-AC09-08SR22470 awarded by the United States Department of Energy. The Government has certain rights in the invention.

FIELD OF THE INVENTION

This invention is directed towards a monitoring system for detection of biological, chemical, and radiological agents. While such agents are encompassed within the field of Weapons of Mass Effects (WME), the present invention is also applicable to the monitoring of other agents including agricultural products, industrial air pollutants, and naturally occurring airborne agents of concern.

BACKGROUND OF THE INVENTION

A variety of monitoring systems is known in the art for both delayed and real time detection of airborne and water borne chemical, radiological, and pathogenic microorganisms. Heretofore, such monitoring systems have depended upon the use of discreet and specialized monitoring systems for passive monitoring or the use of manually deployed measuring devices or detectors in response to a perceived threat. Various detectors include film filters and semi-permeable membrane devices for detecting select chemicals. Such filters and detectors may depend upon either high volume of fluid sampling techniques or incorporate specialized sensing molecules which react in the presence of a targeted environmental agent. A limitation of existing technologies is directed to the infrastructure and effort needed to maintain monitoring devices and limitations in acquiring sufficient sampling volume. Accordingly, it remains room for variation and improvement within the art.

SUMMARY OF THE INVENTION

It is one aspect of one of the present embodiments to provide for a fluid sampling process for detection of environmental agents using existing infrastructure in the form of various collectors and/or concentrators of ambient air or water.

It is a further aspect of at least one embodiment of the present invention to provide for an environmental monitoring system which utilizes water cooling towers as a sampling agent for detection of environmental agents.

It is a further and more particular object of at least one aspect of the present invention to provide for a detection of airborne and water borne agents through the sampling of process water. As defined herein, process water includes but is not limited to water associated with cooling towers, fountains, swamp coolers, waterfalls, and similar structures which have an inherent filtering and/or absorbing capability of airborne materials including materials associated with WME as well as dust, plant material including pollen, soil particles, and molds spores.

It is a further aspect of at least one embodiment in the present invention to provide for a monitoring system for environmental agents which may be present in rain, water, atmosphere, or soil.

It is a further aspect of at least one embodiment in the present invention to provide for a monitoring system using multiple cooling towers or other aquatic systems in a given geographical area for source tracking methodology. The pattern of detection could be combined with weather information to determine the source of a released environmental chemical, biological, or radiological agent.

A further aspect of at least one embodiment in the present invention is to provide for a process of using existing aerosol concentrators, such as cooling towers, as a sampling location for monitoring environmental agents.

These and other features, aspects, and advantages of the present invention will become better understood with reference to the following description and appended claims.

BRIEF DESCRIPTION OF THE DRAWINGS

A fully enabling disclosure of the present invention, including the best mode thereof to one of ordinary skill in the art, is set forth more particularly in the remainder of the specification, including reference to the accompanying drawings.

DESCRIPTION OF THE PREFERRED EMBODIMENT

Figure 1:
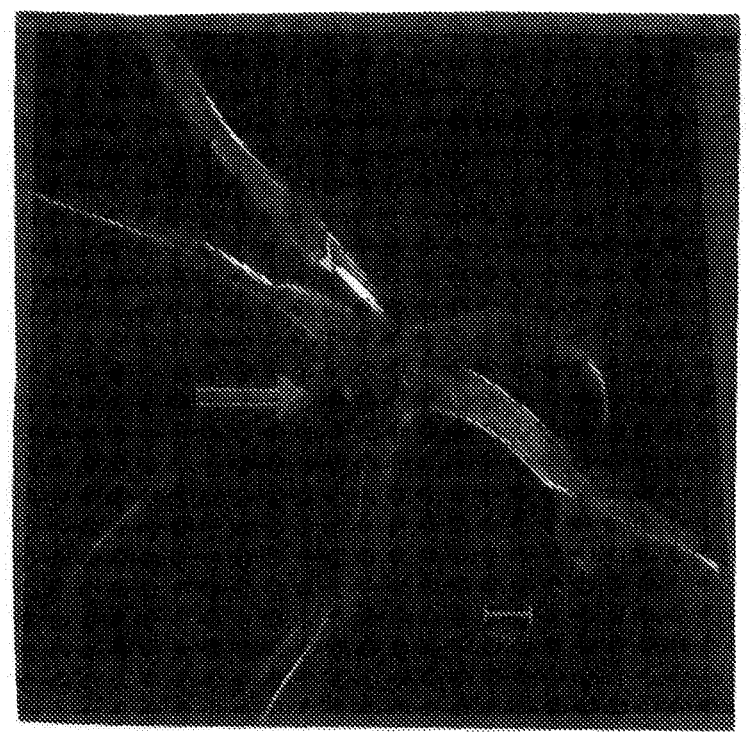
FIG. 1 is a photo micrograph of a pollen grain and fluorescein isocyanate-labeled antibody localized on a *Legionella pneumophila* bacterium (arrow).

Reference will now be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, of which broader aspects are embodied in the exemplary constructions.

In describing the various figures herein, the same reference numbers are used throughout to describe the same material, apparatus, or process pathway. To avoid redundancy, detailed descriptions of much of the apparatus once described in relation to a figure is not repeated in the descriptions of subsequent figures, although such apparatus or process is labeled with the same reference numbers.

As used herein, the term "concentrator" refers to use of aquatic systems which serve to concentrate airborne agents. Such concentrators include water cooling towers, fountains, swamp coolers and waterfalls. Cooling towers for instance can process thousands of cubic feet of air per minute through the use of process water to achieve industrial cooling. In accordance of the present invention, the process water can provide a basis of collection fluid as part of an ongoing environmental monitoring for chemical, biological, and radiological agents.

As used herein, the term "sample concentrator" refers to use of filtration systems designed to increase a concentration of an airborne agent within a retentate such that the retentate or filtrate will contain a detectable level of the airborne agent that might not otherwise be detectable in the base sample.

Industrial concentrators are widely distributed through all industrial populated communities. For instance, cooling towers are associated with any number of heat removal devices used to transfer process heat to the atmosphere. Frequently, cooling towers use the evaporation of water to remove process heat and to cool a working fluid to a near wet-bulb air temperature or utilize recalculating air to cool a working fluid to a near dry-bulb air temperature. For instance, cooling towers which utilize ambient air in association with evaporative water are commonly associated with oil refineries, chemical plants, power stations, and large building Heating, Ventilation, and Air Conditioning (HVAC) equipment. The water utilized in such cooling towers can range from a capacity of under 100 gallons to cooling towers which have a capacity for thousands of gallons.

Numerous examples of cooling towers are known in the art. Represented samples include cooling towers as demonstrated in U.S. Pat. No. 4,094,937 assigned to Zurn Industries and U.S. Pat. No. 4,243,095 assigned to Lummus Company Inc. and which are incorporated herein by reference in their entirety for all purposes.

In the course of this invention, it has been found that cooling towers serve as concentrators for airborne materials such that a water collection basin associated with a cooling tower can provide for an aqueous medium which effectively concentrates airborne agents. The concentration of the airborne agent facilitates the detection of various agents. Cooling towers can be observed on the roofs of tall building as well as at ground level depending on the HVAC system (or other industrial process to which they are integrated). The detection can be based on a strict presence/absence of an environmental agent or a WME biological weapon's agent such as *Bacillus anthracis* (anthrax). The cooling towers also provide for a long term monitoring source of other airborne agents including chemical pollutants, such that usual trends can be detected. The widespread number of collectors within an urban environment can also help with mapping an airborne plume and distribution pattern of various environmental agents of interest.

Various environmental agents can include radionuclides which may be associated with a detonated nuclear device, a dirty bomb or an unintended release from various medical, military, or waste material/production facility.

Certain chemical agents such as the nerve gas sarin, are either detectable in water or hydrolyzed to toxic or non-toxic, yet analytically useful detectable or signature derivatives. Accordingly, hydrolyzed byproducts of certain chemical agents may be evaluated in various collector fluids.

As used therein, the term "agents" with respect to chemical, radiological, biological, and pathogenic agents is broadly defined to include agents that may have a detrimental impact to an individuals' health or a detrimental impact to an ecosystem including, but not limited to, agricultural animals and plants, food supplies, water supplies, and air quality.

For instance, certain chemical agents of interest may include the family of phosphonofluoridates, and which includes Sarins (O-Isopropyl methylphosphonofluoridate), Soman (O-Pinacolyl methylphosphonofluoridate, phosphoramidocyanidates), Tabuns (O-Ethyl N,N-dimethylphosphoramidocyanidate), phosphonothiolates and corresponding alkylated or protonated salts, VX (O-Ethyl S-2-diisopropylaminoethyl methylphosphonothiolate) various sulfur mustards including the group of 2-Chloroethylchloromethylsulfide, Mustard gas Bis(2-chloroethyl)sulfide, Bis (2-chloroethylthio)methane, Sesquimustard 1,2-Bis(2-chloroethylthio)ethane, 1,3-Bis(2-chloroethylthio)-n-propane, 1,4-Bis(2-chloroethylthio)-n-butane, 1,5-Bis(2-chloroethylthio)-n-pentane, Bis(2-chloroethylthiomethyl)ether, O-Mustard: Bis(2-chloroethylthioethyl)ether; various Lewistes including Chlorovinyldichloroarsine, Bis(2-chlorovinyl) chloroarsine, Tris(2-chlorovinyl)arsine; various nitrogen mustards including: Bis(2-chloroethyl)ethylamine, Bis(2-chloroethyl)methylamine, Tris(2-chloroethyl)amine; Saxitoxin and Ricin.

Various chemical agents can also include chemical precursors to further chemical agents and may include the families of aminoethylphosphonite, Alkyl phosphonyldifluorides such as Methylphosphonyl difluoride, O-Alkyl O-2-dialkyl aminoethyl alkyl phosphonites and corresponding alkylated or protonated salts, such as O-Ethyl O-2-diisopropylaminoethyl methylphosphonite, Chlorosarin: O-Isopropyl methylphosphonochloridate, and Chlorosoman: O-Pinacolyl methylphosphonochloridate.

Additional chemical agents of interest may also include Amiton: O,O-Diethyl S-(2-(diethylamino)ethyl)phosphorothiolate and corresponding alkylated or protonated salts, PFIB: 1,1,3,3,3-Pentafluoro-2-(trifluoromethyl)-1-propene, 3-Quinuclidinyl benzilate (BZ), Methylphosphonyl dichloride, Dimethyl methylphosphonate, N,N-Dialkyl phosphoramidic dihalides, Dialkyl N,N-dialkyl phosphoramidates, Arsenic trichloride, 2,2-Diphenyl-2-hydroxyacetic acid, Quinuclidin-3-ol, N,N-Dialkyl (Me, Et, n-Pr or i-Pr) aminoethyl-2-chlorides and corresponding protonated salts, N,N-Dialkyl (Me, Et, n-Pr or i-Pr) aminoethane-2-ols and corresponding protonated salts, N,N-Dialkyl (Me, Et, n-Pr or i-Pr) aminoethane-2-thiols and corresponding protonated salts, Thiodiglycol: Bis(2-hydroxyethyl)sulfide, Pinacolyl alcohol: 3,3-Dimethylbutan-2-ol, Phosgene: Carbonyl dichloride. Cyanogen chloride, Hydrogen cyanide, Chloropicrin: Trichloronitromethane, Phosphorus oxychloride, Phosphorus trichloride, Phosphorus pentachloride, Trimethyl phosphite, Triethyl phosphite, Dimethyl phosphite, Diethyl phosphite, Sulfur monochloride, Sulfur dichloride, Thionyl chloride, Ethyl diethanolamine, Methyl diethanolamine, Triethanolamine, Thiodiglycol, Phosphorus oxychloride, Dimethyl methylphosphonate, Methylphosphonyl difluoride (DF), Methylphosphonyl dichloride (DC), Dimethyl phosphite (DMP), Phosphorus trichloride, Trimethyl phosphite (TMP), Thionyl chloride, 3-Hydroxy-1-methylpiperidine, N,N-Diisopropyl-(beta)-aminoethyl chloride, N,N-Diisopropyl-(beta)-aminoethane thiol, 3-Quinuclidinol, Potassium 2-Chloroethanol fluoride, Dimethylamine, Diethyl ethylphosphonate, Diethyl N,N-dimethylosphoramidate, Diethyl phosphate, Dimethylamine hydrochloride, Ethylphosphinyl dichloride, Ethylphosphonyl dichloride, Ethylphosphonyl difluoride, Methyl benzilate, Methylphosphinyl dichloride, N,N-Diisopropyl-(beta)-amino-ethanol, Pinacolyl alcohol, O-Ethyl 2-diisopropylaminoethyl methylphosphonite (QL), Triethyl phosphate, Arsenic trichloride, Benzilic acid, Diethyl methylphosphonite, Dimethyl ethylphosphonate, Ethylphosphinyl difluoride, Methylphosphinyl difluoride, 3-Quinuclidone, Phosphorus pentachloride, Pinacolone, Potassium cyanide, Potassium bifluoride, Ammonium bifluoride, Sodium bifluoride, Sodium fluoride, Sodium cyanide, Triethanolamine, Phosphorus pentasulphide, Diisopropylamine, Diethylaminoethanol, Sodium sulphide, Sulphur monochloride, Sulphur dichloride, Triethanolamine hydrochloride, N,N-Diisopropyl-2-aminoethyl chloride hydrochloride, Methylphosphonic acid, Diethyl methylphosphonate, N,N-Dimethylaminophosphoryl dichloride, Triisopropyl phosphate, Ethyldiethanolamine, O,O-Diethyl phosphorothioate, O,O-Diethyl phosphorodithioate, Sodium hexafluorosilicate, and Methylphosphonothioic dichloride.

Non-limiting examples of biological agents and/or pathogenic microorganisms may include viruses such as Andes virus, Chapare virus, Chikungunya virus, Choclo virus, Congo-Crimean haemorrhagic fever virus, Dengue fever virus, Dobrava-Belgrade virus, Eastern equine encephalitis virus, Ebola virus, Guanarito virus, Hantaan virus, Hendra virus (Equine morbillivirus), Japanese encephalitis virus, Junin virus, Kyasanur Forest virus, Laguna Negra virus, Lassa fever virus, Louping ill virus, Lujo virus, Lymphocytic choriomeningitis virus, Machupo virus, Marburg virus, Monkey pox virus, Murray Valley encephalitis virus, Nipah virus, Omsk haemorrhagic fever virus, Oropouche virus, Powassan virus, Rift Valley fever virus, Rocio virus, Sabia virus, Seoul virus, Sin nombre virus, St Louis encephalitis virus, Tick-borne encephalitis virus (Russian Spring-Summer encephalitis virus), Variola virus, Venezuelan equine encephalitis virus, Western equine encephalitis virus, Yellow fever virus; various bacteria such as *Bacillus anthracis, Brucella abortus, Brucella melitensis, Brucella suis, Chlamydophila psittaci* (formerly known as *Chlamydia psittaci*), *Clostridium botulinum, Francisella tularensis, Burkholderia mallei* (*Pseudomonas mallei*), *Burkholderia pseudomallei* (*Pseudomonas pseudomallei*), *Salmonella typhi, Shigella dysenteriae, Vibrio cholerae, Yersinia pestis, Clostridium perfringens*, epsilon toxin producing types, Enterohaemorrhagic *Escherichia coli*, serotype O157 and other verotoxin producing serotypes, *Coxiella burnetii, Rickettsia prowazekii* and various toxins such as Botulinum toxins, *Clostridium perfringens* toxins, Conotoxin, Ricin, Saxitoxin, Shiga toxin, *Staphylococcus aureus* toxins, Tetrodotoxin, Verotoxin and shiga-like ribosome inactivating proteins, Microcystin (Cyanginosin), Aflatoxins, Abrin, Cholera toxin, Diacetoxyscirpenol toxin, T-2 toxin, HT-2 toxin, Modeccin toxin, Volkensin toxin, Viscum Album Lectin 1 (Viscumin) and fungi *Coccidioides immitis, Coccidioides posadasii.*

Various agents of interest may also include animal and plant pathogens including African swine fever virus, Avian influenza virus, Bluetongue virus, Foot and mouth disease virus, Goat pox virus, Herpes virus (Aujeszky's disease), Hog cholera virus (synonym: swine fever virus), Lyssa virus, Newcastle disease virus, Peste des petits ruminants virus, Porcine enterovirus type 9 (synonym: swine vesicular disease virus), Rinderpest virus, Sheep pox virus, Teschen disease virus, Vesicular stomatitis virus, Lumpy skin disease virus, African horse sickness virus, *Mycoplasma mycoides* subspecies *mycoides* SC (small colony), *Mycoplasma capricolum* subspecies *capripneumoniae* ("strain F38"), *Xanthomonas albilineans, Xanthomonas campestris* pv. Citri, *Xanthomonas oryzae* pv. oryzae (*Pseudomonas campestris* pv. oryzae), *Clavibacter michiganensis* subsp. *sepedonicus* (*Corynebacterium michiganensis* subsp. *sepedonicum* or *Corynebacterium sepedonicum*), Ralstonia solanacearum races 2 and 3 (*Pseudomonas* solanacearum races 2 and 3 or *Burkholderia* solanacearum races 2 and 3), *Colletotrichum* coffeanum var. virulans (*Colletotrichum kahawae*), *Cochliobolus miyabeanus* (*Helminthosporium oryzae*), *Microcyclus ulei* (syn. *Dothidella ulei*), *Puccinia graminis* (syn. *Puccinia graminis* f. sp. *tritici*), *Puccinia striiformis* (syn. *Puccinia glumarum*), *Pyricularia grisea/Pyricularia oryzae*, Potato Andean latent tymovirus, Potato spindle tuber viroid.

Radiological agents may include Tritium ($H^3$), Cesium (Cs, Uranium (U), Strontium (Sr), Plutonium, (Pu), and/or Iodine (I).

The above examples are not designed to be limitations on the agents of interest. Rather, they are representative of the type of chemical, radiological and biological agents of interest which are suitable for detection through the various collectors and methodology identified herein. One having ordinary skill in the art would recognize the most appropriate analytical assays for the various agents of interest in order to use collectors as a monitoring source for evaluating the presence of the various aspects of interest.

In addition to initial detection of an airborne agent, the collectors described herein could also be used as a monitoring system following clean up or remediation of an environmental agent. A useful component of the present invention is a widespread number of collectors which can be sampled and monitored. The use of this infrastructure reduces the expense and logistical difficulty of maintaining discreet or dedicated monitors.

The present invention also lends itself to mobile deployment where a portable unit such as a modified swamp cooler could be placed in a specific location to monitor ambient air where existing cooling towers or fountains were not available. An example of one suitable swamp cooler is seen in U.S. Pat. No. 5,383,337 and which is incorporated herein by reference in its entirety for all purposes.

While cooling towers can be classified several ways, the main categories are dry towers and wet towers, as well as some hybrid wet-dry combinations. Wet, or evaporative cooling towers are the predominant type worldwide and the focus of this application. In cooling towers a reservoir of cooling water is used to remove process heat in combination with large fans. The water now containing the process heat is sprayed or released as an aerosol against a countercurrent of ambient blown air. While some water vapor is removed by evaporation and aerosol drift, a large percentage of the water is recirculated to a catch basin. The catch basin of process water thereby concentrates airborne agents which are introduced or entrained into the water by the ambient air. By sampling the basin water, the presence and relative concentration of various environmental agents can be detected and/or monitored.

Example 1

Water from an industrial cooling tower at the Savannah River National Laboratory was used as a source of concentrator fluid. Sampling of the water from the cooling tower, compared to a source and supply of water used for the cooling tower, indicated the presence of pollen within the cooling water. The presence of the pollen is evidence that the cooling water serves as a collector for airborne agents such as pollen.

It is further noted that the pollen itself can serve as a secondary collector in that many environmental agents will absorb to pollen. As the pollen is subsequently collected and concentrated within a water cooler, the carrier material such as bacteria, a radionuclide, or other organic material is likewise present and concentrated within the cooling tower water. As such, the cooling tower water provides for a collection medium for the collective for various environmental agents. Some environmental agents, such as pollen, are themselves serving as collectors for other environmental agents. Ultimately, the presence of various environmental agents is concentrated within the cooling water and thereby is detectable.

As seen in reference to FIG. 1, a photo micrograph of a pollen grain is seen in which an environmental agent in the form of a *Legionella* sp. was captured on the pollen grain. The *Legionella* is visualized by fluorescein isocyanate-labeled antibodies. The binding of the bacteria is most likely occurring after the pollen enters the cooling tower.

Figure 2:
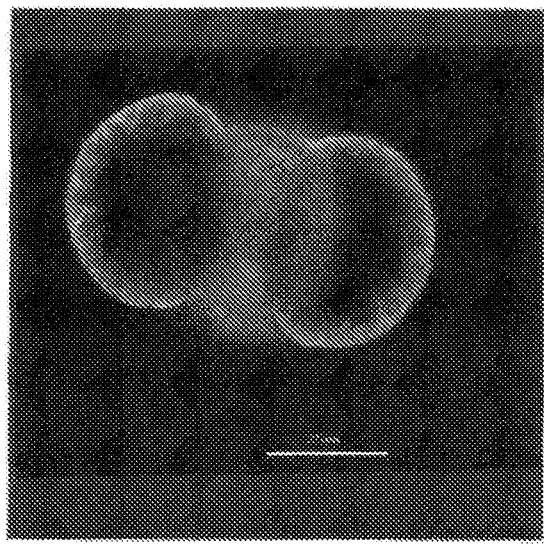
FIG. 2 is a photo micrograph of pollen isolated within water contained within a cooling tower.

As seen in reference to FIG. 2, a *Legionella* species, from a 500 milliliter water sample collected from a Savannah River National Laboratory Cooling Tower, is visualized by fluorescein isocyanate-labeled antibody to *Legionella* species. The screening techniques of using cooling tower water as an assay medium can be conducted with any number of bacterial specific labeled antibodies or various ligands which are coupled to markers to assist in visualization using various forms of microscopy. While the *Legionella* species are known to colonize cooling towers and similar equipment, the screening process can be carried out with any number of bacteria or other biological agents of interest such as various *Bacillus* species associated with anthrax. Similar antibody detection methods directed to either anthrax spores or the *Bacillus* organism could be utilized in a similar manner in order to monitor for known pathogens.

Example 2

Figure 3:
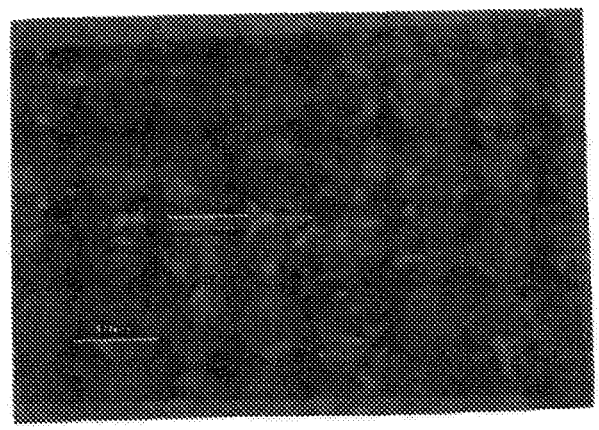
FIG. 3 is a fluorescein isocyanate-labeled *Legionella pneumophila* concentrated from water samples in a cooling tower and collected onto a membrane filter.
Figure 4A:
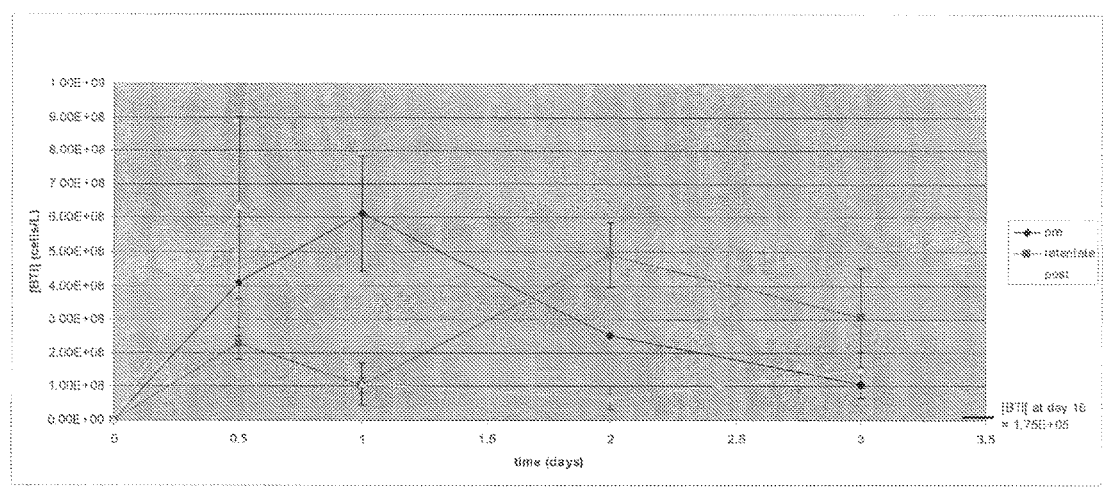
FIGS. 4A-4C set forth data from a cooling tower with respect to detection of *Bacillus thuringiensis* which was applied as an aerosol in proximity to a cooling tower.
Figure 4B:
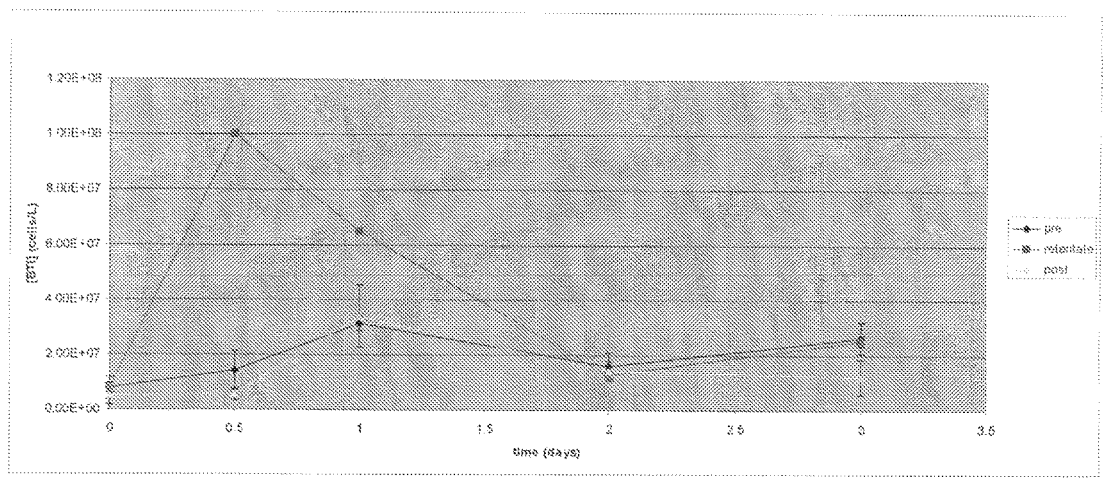
Figure 4C:
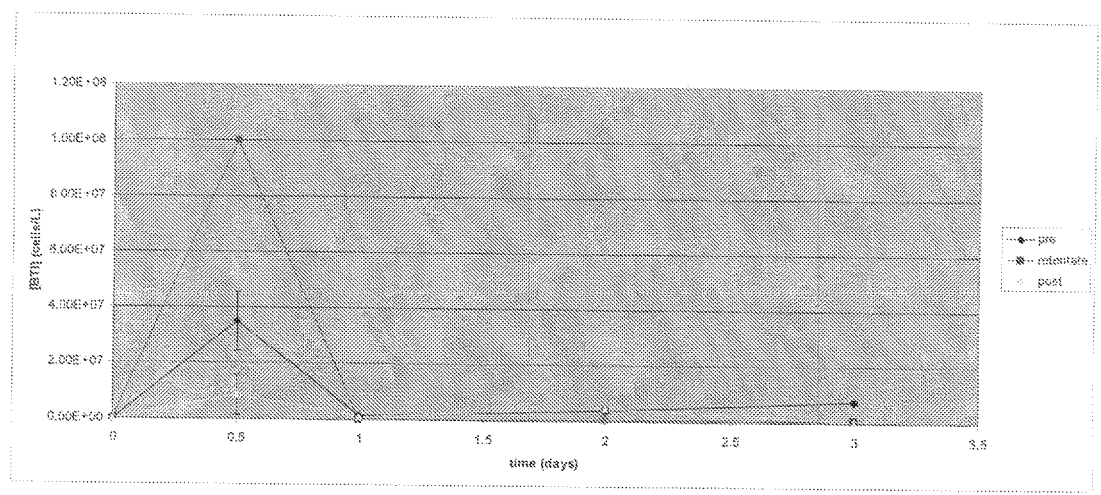

In reference to FIGS. 4A through 4C, the evaporative cooling towers were used to collect samples following an aerosolized release of a pesticide grade *Bacillus thuringiensis* (BTI) which was released in proximity to the cooling tower. A Hurricane™ ultra blower is used to distribute the bacteria in keeping with standard application and dispersion rates. As set forth in FIGS. 3A through 3C, at time zero BTI were detected within samples as originally collected (pre) and when concentrated within retentate.

Example 3

Cooling towers and other concentrators can be utilized to provide liquid samples for various biological, radionuclide, and chemical detection. Water samples have been taken from a cooling tower in proximity to a former nuclear material processing facility at the Department of Energy Savannah River Site (SRS), in Aiken, S.C. SRS is a former nuclear material production facility or an area where there are background concentrations of certain metals and ions. Samples of an original collected concentration as well as a retentate concentration were obtained and values for various elements were conducted. The concentrated retentate was obtained by using a portable multi-use automated concentration system which directed samples through a 0.2 µM filtration system. Several passes through the filtration system were made more to obtain a suspension which would include a concentration of any particulates present in the original solution. The results of the analysis are shown in Table 1 for both the original concentration cooling water tower as well as a concentrated retentate. A number of elements were present in the cooling water at levels which were below detectable values initially. By using a sample concentrator, detection techniques allowed for a determination that various elements were present. Results illustrate that water in cooling towers are used to monitor airborne chemical compounds associated with particles. The use of a filtration type solution concentrator allows for improved detection levels. Ion chromatography-mass spectrometry (ICP-MS) was used for water and retentate sample analysis.

TABLE 1

Comparison of ICP-MS results from unconcentrated cooling tower water compared to retentate from PMACS concentrated samples.

| Element ID | Mass (amu) | Cooling Tower water concentration (ppm) | Retentate concentration (ppm) | Concentration Factor by retentate |
|---|---|---|---|---|
| Cobalt | 59 | BD | 5.70E−02 | 1.43 |
| Rubidium/ Molybdenum | 98 | BD | 4.60E−02 | 1.54 |
| Cesium | 133 | 9.61E−01 | 2.57E+00 | 2.67 |
| Barium | 135 | BD | 3.20E−02 | 1.61 |
| Barium | 137 | BD | 5.80E−02 | 1.94 |
| Lanthinum/ Cesium/Barium | 138 | BD | 3.21E−01 | 2.31 |
| Lead | 206 | BD | 1.85E−01 | 9.30 |

Various conventional techniques can be used for sampling of the water. For instance, filter membranes can be used to capture for subsequent analysis of various chemical constituents, bacteria and other targeted environmental agents. Charcoal filters could be specifically used for organic chemical agent concentration and detection. Simultaneously zeolite containing filters could be used for the collection and subsequent detection of elemental and organic forms of radioactive Iodine. As well, other types of specific ion exchange and similar resins can be used to extract organic and inorganic agents of interest, e.g. toxins or select chemical species, from the process water. In addition, microscopic examination of collected water and/or membrane filter material can also be used including epifluorescent microscopy and the use of fluorescent labeling molecules which can be employed for visualization of microorganisms by epifluorescent microscopy. Also, samples can be processed for molecular detection methodologies not limited to polymerase chain reaction (PCR)-based methods for microorganisms and other analytical techniques such as high pressure liquid chromatography, gas chromatography, proteomics, lipid analyses, mass spectrometry etc.

The use of the aquatic collectors and the analytical techniques described herein lend themselves to a useful process of mapping one or more airborne agents. For instance, in a suspected release zone of an airborne agent, multiple collectors can be assayed for the airborne agent to determine contamination distribution. Such information can determine possible sources and/or release points of an airborne agent and can determine areas of exposure based upon the presence/absence within collectors. In addition, data from multiple collectors can be used to approximate relative concentrations of the airborne agent. Such information, when visually mapped, can provide useful information for the airborne agent including, but not limited to release points, areas of exposure and plume migration patterns, and provide initial data on relative concentrations. This information can be beneficial to clean up efforts and risk assessment for areas which have been exposed to the airborne agent.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the claims of the present invention. In addition, it should be understood that aspects of the various embodiments may be interchanged, both in whole, or in part. Therefore, the spirit and scope of the invention should not be limited to the description of the preferred versions contained therein.

The invention claimed is:

1. The process of detecting an airborne agent comprising:
    using a countercurrent cooling tower as an airborne agent concentrator;
    taking a sample of process water and/or biofilm from a water collection basin of the countercurrent cooling tower, the process water being water that has been sprayed into a current of air and collected into the water collection basin for recirculation such that at least a portion of any airborne agents within the air becomes entrained in the process water and/or biofilm collected in the water collection basin so that any such airborne agents become more concentrated in the process water and/or biofilm in the water collection basin; and
    evaluating the sample concentrated by the cooling tower for the presence of an airborne agent within the air around the cooling tower without passing the sample through a sample concentrator.

2. The process according to claim 1 wherein the airborne agent is selected from the group consisting of chemical agents, biological agents, and radiological agents.

3. The process according to claim 2 wherein the biological agent is an anthrax species.

4. The process according to claim 2 wherein the radiological agent is selected from the group consisting of Tritium ($H^3$), Cesium (Cs, Uranium (U), Strontium (Sr), Plutonium, (Pu), Iodine (I) and combinations thereof.

5. The process of mapping an airborne agent contamination plume comprising;
    using a plurality of aquatic concentrators as airborne agent concentrators;
    collecting a plurality of samples of process water from collection basins in the plurality of aquatic concentrators that spray the process water into air and collect at least a portion of the process water for recirculation such that at least a portion of any airborne agents within the air becomes entrained in the process water collected for recirculation in the collection basins so that any such airborne agents become more concentrated in the process water that is collected in the collection basins in the aquatic concentrators, the aquatic concentrators being present within a known geographic location;
    evaluating each sample concentrated by the respective aquatic concentrator for the presence of an airborne agent; and
    combining data from each sample to determine a geographical distribution of at least one of the airborne agents,
    wherein the evaluating step comprises evaluating each sample concentrated by the respective aquatic concentrator for the presence of an airborne agent without passing the sample through a sample concentrator.

6. The process according to claim 5 wherein the step of combining the sample data further includes determining relative levels of airborne agents based upon detected levels of an airborne agent present within the aquatic concentrator.

7. The process according to claim 2 wherein the chemical agent is lead (Pb).

8. The process of mapping airborne agents comprising;
    using a plurality of cooling towers as airborne agent concentrators;
    selecting the plurality of cooling towers within a geographic territory of interest, each cooling tower having a water collection basin containing process water collected for recirculation from being sprayed against a countercurrent flow of ambient air such that at least a portion of any airborne agents within the air becomes entrained in the process water collected in the water collection basin so that any such airborne agents become more concentrated in the process water in the water collection basin;
    taking a sample of the process water from the water collection basin of each of the plurality of cooling towers concentrated by the respective cooling tower;
    evaluating the taken samples for the presence of an airborne agent; mapping a location of airborne agents of interest detected from the plurality of cooling towers,
    wherein the evaluating step comprises evaluating the taken samples without passing the sample through a sample concentrator.

9. The process according to claim 8 wherein said step of taking a sample of the process water from the water collection basin further comprises taking a sample of process water that includes material selected from the group consisting of mold spores, pollen, plant material, dust and soil particles.

10. The process according to claim 8 wherein the evaluating step is a qualitative assay.

* * * * *